United States Patent [19]

Wismer

[11] Patent Number: 4,950,364

[45] Date of Patent: Aug. 21, 1990

[54] PROCESS FOR THE SEPARATION OF 1,1-DICHLORO-1-FLUOROETHANE AND 1,1,1,3,3-PENTAFLUOROBUTANE

[75] Inventor: John A. Wismer, Devon, Pa.

[73] Assignee: Pennwalt Corporation, Philadelphia, Pa.

[21] Appl. No.: 347,603

[22] Filed: May 4, 1989

[51] Int. Cl.$^5$ .......................... B01D 3/38; C07C 17/38
[52] U.S. Cl. .......................... 203/50; 203/74; 203/81; 203/98; 570/164; 570/178
[58] Field of Search .......................... 203/39, 50, 81, 82, 203/98, 74, 75, 77; 570/178, 163, 164–169

[56] References Cited

U.S. PATENT DOCUMENTS

| | | | |
|---|---|---|---|
| 2,146,354 | 2/1939 | Scherer | 570/164 |
| 2,450,414 | 10/1948 | Benning | 570/178 |
| 2,549,609 | 4/1951 | Johnson | 570/178 |
| 3,689,374 | 9/1972 | Hanson | 570/178 |
| 3,833,676 | 9/1974 | Ukaji et al. | 570/164 |

Primary Examiner—Wilbur Bascomb
Attorney, Agent, or Firm—Seidel, Gonda, Lavorgna & Monaco

[57] ABSTRACT

1,1-Dichloro-1-fluroethane and 1,1,1,3,3-pentafluorobutane are separated from their liquid mixtures, such as liquid mixtures resulting from the hydrofluorination of 1,1,1-trichloroethane or vinylidene chloride. 1,1-Dichloro-1-fluoroethane and 1,1,1,3,3-pentafluorobutane are completely separated by distillation, by adding to the mixture thereof a liquid containing at least about 3 moles of hydrogen fluoride per mole of 1,1-dichloro-1-fluoroethane in the mixture subject to separation.

12 Claims, 1 Drawing Sheet

PROCESS FOR THE SEPARATION OF 1,1-DICHLORO-1-FLUOROETHANE AND 1,1,1,3,3-PENTAFLUOROBUTANE

FIELD OF THE INVENTION

The invention relates to the separation of 1,1-dichloro-1-fluoroethane from its mixtures with 1,1,1,3,3-pentafluorobutane, particularly from such mixtures resulting from the manufacture of 1,1-dichloro-1-fluoroethane and/or 1-chloro-1,1-difluoroethane, by the hydrofluorination of 1,1,1-trichloroethane or vinylidene chloride.

BACKGROUND OF THE INVENTION

The hydrofluorination of 1,1,1-trichloroethane to form 1,1-dichloro-1-fluoroethane and 1-chloro-1,1-difluoroethane generates 1,1,1,3,3-pentafluorobutane (hereinafter "pentafluorobutane") as a by-product. While pentafluorobutane is generated only in small amounts, typically about 0.5 wt% based upon the amount of 1,1-dichloro-1-fluoroethane product, pentafluorobutane and 1,1-dichloro-1-fluoroethane have very similar boiling points, respectively 40° C. and 32° C. They also form an azeotrope, having a composition of about 19 mol% pentafluorobutane and 81 mol% 1,1-dichloro-1-fluoroethane. Thus, separation of pentafluorobutane from 1,1-dichloro-1-fluoroethane by simple distillation is not feasible. A significant loss of 1,1-dichloro-1-fluoroethane would result from distilling the pentafluorobutane/1,1-dichloro-1-fluoroethane azeotrope since the composition of the azeotrope is about 19 mol% pentafluorobutane to 81 mol% 1,1-dichloro-1-fluoroethane.

SUMMARY OF THE INVENTION

A process for separating 1,1-dichloro-1-fluoroethane from its liquid mixtures with pentafluorobutane is provided. The liquid mixture is separated by distillation to obtain a top product comprising a mixture of hydrogen fluoride and 1,1-dichloro-1-fluoroethane and a bottom product comprising pentafluorobutane, by adding to the mixture a liquid containing at least about 3 moles of hydrogen fluoride per mole of 1,1-dichloro-1-fluoroethane in the mixture.

DETAILED DESCRIPTION OF THE INVENTION

Figure 1:
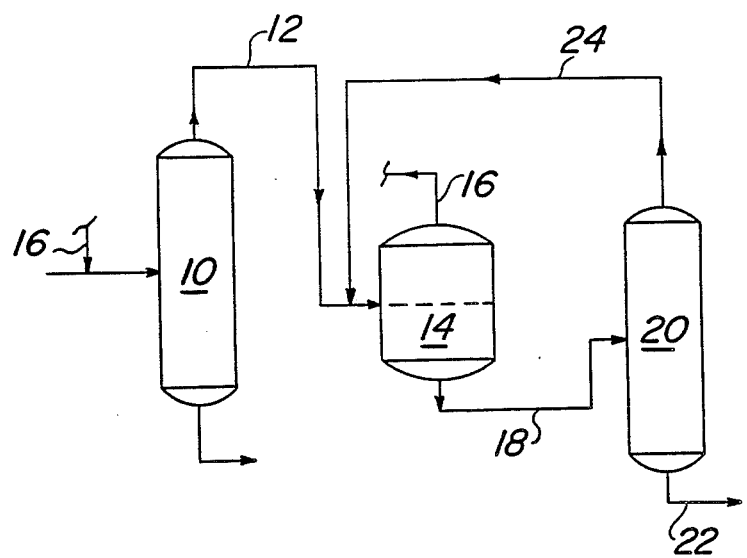
FIG. 1 is a schematic illustrating an embodiment of the process of the invention.

The present separation process finds utility in the manufacture of halohydrocarbons wherein mixtures of 1,1-dichloro-1-fluoroethane and pentafluorobutane may be formed. The process is particularly useful in separating such liquid mixtures of 1,1-dichloro-1-fluoroethane and pentafluorobutane which may be formed in the manufacture of 1,1-dichloro-1-fluoroethane and/or 1-chloro-1,1-difluoroethane. Such mixtures are formed as a consequence of the reaction of hydrogen fluoride in a hydrofluorination reaction mixture with 1,1,1-trichloroethane or vinylidene chloride.

I have found that the azeotrope formed by 1,1-dichloro-1-fluoroethane and pentafluorobutane may be broken by adding to mixtures thereof a liquid containing at least about 3 moles of hydrogen fluoride per mole of 1,1-dichloro-1-fluoroethane in the mixture. The hydrogen fluoride must be added in an amount of at least 3 times the molar amount of 1,1-dichloro-1-fluoroethane in the mixture subject to separation since, in the distillation of the mixture, for every mole of 1,1-dichloro-1-fluoroethane carried overhead, at least 3 moles of hydrogen fluoride are carried overhead. The addition of hydrogen fluoride to the mixture permits complete separation of pentafluorobutane and 1,1-dichloro-1-fluoroethane by simple distillation.

The liquid added to the mixture of pentafluorobutane and 1,1-dichloro-1-fluoroethane to facilitate their separation may comprise pure hydrogen fluoride, or a mixture of hydrogen fluoride with other compounds. Thus, in addition to hydrogen fluoride, the liquid added according to the present invention may contain, for example, 1,1-dichloro-1-fluoroethane or 1-chloro-1,1-difluoroethane without any disadvantage. The liquids which may be used include the reaction product originating from the hydrofluorination of 1,1,1-trifluoroethane or vinylidene chloride.

The mixture subject to separation may contain large amounts of 1,1-dichloro-1-fluoroethane, variable amounts of starting organic reactant (vinylidene chloride or 1,1,1trifluoroethane) and smaller amounts of the product 1-chloro-1,1-difluoroethane, in addition to hydrogen fluoride. When the mixture originates from the hydrofluorination of vinylidene chloride or 1,1,1-trifluoroethane, it is advantageous to remove at least part of the hydrogen chloride by-product from the mixture, for example, by distillation, before treating it according to the separation process of the present invention.

If, after separation of hydrogen chloride, the mixture subject to separation already contains at least 3 moles of hydrogen fluoride per mole of 1,1-dichloro-1-fluoroethane in the mixture, the mixture can be separated directly by distillation to obtain a top product comprising a mixture of hydrogen fluoride and 1,1-dichloro-1-fluoroethane, and a bottom product comprising pentafluorobutane, without adding additional hydrogen fluoride. If the mixture contains hydrogen fluoride in an amount of less than 3 moles per mole of 1,1-dichloro-1-fluoroethane, additional hydrogen fluoride must be added.

According to the process of the invention, a mixture containing 1,1-dichloro-1-fluoroethane and pentafluorobutane, from which it is desired to separate said 1,1-dichloro-1-fluoroethane from pentafluorobutane, is combined with or already has contained therein, an amount of hydrogen fluoride equal to at least three times the amount of 1,1-dichloro-1-fluoroethane contained in the mixture subject to separation, on a molar basis. The mixture is subjected to a distillation which results in the formation of a top product comprising hydrogen fluoride and 1,1-dichloro-1-fluoroethane, and a bottom product comprising pentafluorobutane. Preferably, the top product of 1,1-dichloro-1-fluoroethane and hydrogen fluoride has a composition similar to the azeotropic composition thereof, i.e., about 35 wt.% hydrogen fluoride and about 65 wt.% 1,1-dichloro-1-fluoroethane, corresponding to about 76 mol% hydrogen fluoride and about 24 mol% 1,1-dichloro-1-fluoroethane. The term "azeotrope" or "azeotropic composition" as used herein refers not only to liquids comprising one phase, i.e., homoazeotropes, but also includes two-phase liquids, i.e., heteroazeotropes, such as the aforesaid mixture of hydrogen fluoride and 1,1-dichloro-1-fluoroethane.

The distillation is carried out in a distillation column having a temperature at the column top of preferably no higher than about 50° C. Reaction between hydrogen fluoride and 1,1-dichloro-1-fluoroethane, which forms the more fluorinated product, 1-chloro-1,1-difluoroethane, is minimized by maintaining the distillation temperature below 50° C. At this temperature, the column pressure is about 48 PSIG. Correspondingly, at the more preferred column top temperature of 30° C., the column pressure is about 18 PSIG.

The distillation top product is condensed to form a liquid condensate, which is then separated by phase separation into a liquid organic phase enriched in 1,1-dichloro-1-fluoroethane relative to hydrogen fluoride and a liquid inorganic phase enriched in hydrogen fluoride relative to 1,1-dichloro-1-fluoroethane. Separation may be carried out in accordance with various techniques well-known to those skilled in the art. Separation may be carried out, for example, by means of an ordinary condenser/decanter. The phase separation is generally performed at a temperature low enough to minimize the reactivity and solubility of hydrogen fluoride and 1,1-dichloro-1-fluoroethane. The phase separation is most advantageously conducted at a temperature of from about −25° C. to about −15° C. in the phase separator. At this temperature, hydrogen fluoride readily separates from its mixture with 1,1-dichloro-1-fluoroethane. Phase separation in this manner results in an upper liquid phase enriched in hydrogen fluoride relative to 1,1-dichloro-1-fluoroethane, and a lower liquid phase enriched in 1,1-dichloro-1-fluoroethane relative to hydrogen fluoride.

By way of illustration, and not by limitation, the upper liquid phase may comprise about 92 wt.% hydrogen fluoride and about 8 wt.% 1,1-dichloro-1-fluoroethane, while the lower liquid phase may comprise about 1 wt.% hydrogen fluoride and about 99 wt.% 1,1-dichloro-1fluoroethane. The foregoing amounts are intended to be illustrative only.

Separation of the liquid phases is most advantageously carried out by decantation, utilizing any of the available decantation apparatuses which are well-known to those skilled in the art.

The upper liquid phase from the phase separator is enriched in hydrogen fluoride. A stream thereof is thus advantageously recycled to and combined with the liquid mixture of 1,1-dichloro-1-fluoroethane and pentafluorobutane subject to separation, prior to the liquid mixture's distillation. Thus, in this manner, the amount of hydrogen fluoride in the mixture may be increased to achieve separation of 1,1-dichloro-1-fluoroethane and pentafluorobutane.

Alternatively, the hydrogen fluoride-enriched inorganic liquid phase may be recycled to the feed of a reactor for the production of 1,1-dichloro-1-fluoroethane from the reaction of hydrogen fluoride and 1,1,1trifluoroethane, as in the case where the separation process is coupled with a process for the production of 1,1-dichloro-1-fluoroethane.

The phase separation lower liquid phase, which comprises a 1,1-dichloro-1-fluoroethane-enriched liquid, is advantageously subjected to further treatment in order to separate hydrogen fluoride and 1,1-dichloro-1-fluoroethane. Thus, the 1,1-dichloro1-fluoroethane-enriched liquid is subjected to a distillation which results in a mixture of 1,1-dichloro-1-fluoroethane and hydrogen fluoride as a distillation top product, and 1,1-dichloro-1-fluoroethane as a distillation bottom product. The top product preferably has a composition similar to the azeotropic composition of 1,1-dichloro-1-fluoroethane and hydrogen fluoride. The distillation is carried out in a distillation column having a temperature at the column top preferably no higher than 50° C., in order to minimize reaction of hydrogen fluoride and 1,1-dichloro-1-fluoroethane. Generally, the distillation is carried out using a column top temperature of from about 20° C. to about 50° C.

It should be apparent that the process of the invention for separating 1,1-dichloro-1-fluoroethane and pentafluorobutane may be advantageously coupled with distillations for the separation of 1,1-dichloro-1-fluoroethane and hydrogen fluoride, obtained by the hydrofluorination of vinylidene chloride or 1,1,1-trichloroethane. After separation of hydrogen chloride, the hydrofluorination reaction product mixture is subject to distillation to separate 1,1-dichloro-1-fluoroethane from pentafluorobutane. If the hydrofluorination reaction product already contains 3 moles or more of hydrogen fluoride per mole of 1,1-dichloro-1-fluoroethane, then the reaction product may be subjected to the aforesaid distillation directly without adding additional hydrogen fluoride. Thus, it should be understood that, with reference to the addition of hydrogen fluoride to the mixture of 1,1-dichloro-1-fluoroethane and pentafluorobutane, the expression "adding to the mixture a liquid containing at least about 3 moles of hydrogen fluoride per mole of 1,1-dichloro-1-fluoroethane in the mixture", also includes the situation where no extrinsic hydrogen fluoride is added, as in the case where the mixture already contains 3 or more moles of hydrogen fluoride per mole of 1,1-dichloro-1-fluoroethane.

The process of the invention is illustrated in greater detail in FIG. 1. To a stream containing 1,1-dichloro-1-fluoroethane and pentafluorobutane, hydrogen fluoride is added so that the molar ratio of hydrogen fluoride to 1,1-dichloro-1-fluoroethane in the stream is at least about 3:1. The stream to which hydrogen fluoride has been added (or which already contains the hydrogen fluoride) is subjected to distillation in column 10. Column 10 is operated, for example, at a temperature at the column bottom of about 50° C. and a temperature at the column top of about 45° C., and a pressure of about 40 PSIG. Under these conditions, a mixture of hydrogen fluoride and 1,1-dichloro-1-fluoroethane is obtained overhead. Pentafluorobutane is obtained as the bottom product. The overhead stream is conveyed through line 12 to phase separator 14, which is operated, for example, at a temperature from about −25° C. to about −15° C. The hydrogen fluoride-enriched upper liquid phase is collected in line 16 for recycle to the column 10 feed. The 1,1-dichloro-1-fluoroethane-enriched lower liquid phase is pumped through line 18 to column 20, which is operated, for example, at a temperature at the column top of about 30° C. and a temperature at the column bottom of about 58° C., and a pressure of about 20 PSIG. 1-1-Dichloro-1-fluoroethane is obtained in line 22 as the bottom product. The column 20 top product, comprising an azeotrope of hydrogen fluoride and 1,1-dichloro-1-fluoroethane, is recycled through line 24 and combined with the top product of column 10 for feeding to phase separator 14.

The process of the invention results in complete separation of pentafluorobutane and 1,1-dichloro-1-fluoroethane, utilizing distillation and phase separation techniques which may be advantageously coupled with manufacturing processes for the production of 1,1-dichloro-1-fluoroethane.

The present invention may be embodied in other specific forms without departing from the spirit or essential attributes thereof and, accordingly, reference should be made to the appended claims, rather than to the foregoing specification, as indicating the scope of the invention.

I claim:

1. A process for separating 1,1-dichloro-1fluoroethane from its liquid mixture with 1,1,1,3,3-pentafluorobutane, comprising: separating the liquid mixture by distillation to obtain a top product comprising hydrogen fluoride and 1,1-dichloro-1-fluoroethane, and a bottom product comprising 1,1,1,3,3-pentafluorobutane, by adding to the mixture a liquid containing at least about 3 moles of hydrogen fluoride per mole of 1,1-dichloro-1-fluoroethane in the mixture.

2. A process according to claim 1 wherein the distillation is conducted in a distillation column having a temperature at the column top no higher than about 50° C.

3. A process according to claim 1 wherein the distillation top product has a composition similar to the azeotropic composition of 1,1-dichloro-1-fluoroethane and hydrogen fluoride.

4. A process according to claim wherein the distillation top product is condensed to form a liquid condensate, and the condensate is separated by phase separation into a liquid organic phase enriched in 1,1-dichloro-1-fluoroethane relative to hydrogen fluoride and a liquid inorganic phase enriched in hydrogen fluoride relative to 1,1-dichloro-1-fluoroethane.

5. A process according to claim 4 wherein the phase separation is conducted at a temperature of from about −25° C. to about −15° C.

6. A process according to claim 4 wherein the hydrogen fluoride-enriched inorganic liquid phase is combined with the liquid mixture of 1,1-dichloro-1-fluoroethane and 1,1,1,3,3-pentafluorobutane subject to distillation.

7. A process according to claim 4 wherein the hydrogen fluoride-enriched inorganic liquid phase is recycled to the feed of a reactor for the production of 1,1-dichloro-1-fluoroethane from the reaction of hydrogen fluoride and 1,1,1-trichloroethane.

8. A process according to claim 4 further comprising separating the 1,1-dichloro-1-fluoroethane-enriched liquid organic phase by a second distillation to obtain a mixture of 1,1-dichloro-1-fluoroethane and hydrogen fluoride as a distillation top product, and 1,1-dichloro-1-fluoroethane as a distillation bottom product.

9. A process according to claim 8 wherein the second distillation is conducted in a distillation column having a temperature at the column top no higher than about 50° C.

10. A process according to claim 8 wherein the second distillation top product has a composition similar to the azeotropic composition of hydrogen fluoride and 1,1-dichloro-1-fluoroethane.

11. A process according to claim 8 wherein the second distillation top product is combined with the top product from the distillation of the liquid mixture of 1,1-dichloro-1-fluoroethane and 1,1,1,3,3-pentafluorobutane.

12. A process according to claim 1 wherein the liquid added to the mixture of 1,1-dichloro-1-fluoroethane and 1,1,1,3,3-pentafluorobutane subject to separation is a reaction product originating from the hydrofluorination of 1,1,1-trichloroethane or vinylidene chloride.

* * * * *

UNITED STATES PATENT AND TRADEMARK OFFICE
CERTIFICATE OF CORRECTION

PATENT NO. : 4,950,364

DATED : August 21, 1990

INVENTOR(S) : John A. Wismer

It is certified that error appears in the above—identified patent and that said Letters Patent is hereby corrected as shown below:

Column 2, line 24, change "1,1,1trifluoroethane" to --1,1,1-trifluoroethane--; Column 3, lines 37-38, change "1,1-dichloro-1fluoroethane" to --1,1-dichloro-1-fluoroethane; Column 3, line 57, change "1,1,1trifluoroethane" to --1,1,1-trifluoroethane--; Column 3, line 64, change "1,1-dichloro1-fluoroethane-" to --1,1-dichloro-1-fluoroethane- --; Claim 1, lines 1-2, change "1,1-dichloro-1fluoroethane" to --1,1-dichloro-1-fluoroethane--; Claim 4, line 1, add --1-- after "claim".

Signed and Sealed this

Seventeenth Day of December, 1991

Attest:

HARRY F. MANBECK, JR.

Attesting Officer

Commissioner of Patents and Trademarks